US006458552B1

(12) United States Patent
Fourie et al.

(10) Patent No.: US 6,458,552 B1
(45) Date of Patent: Oct. 1, 2002

(54) METALLOPROTEASE PEPTIDE SUBSTRATES AND METHODS

(75) Inventors: Anne Fourie, Del Mar; Lars Karlsson, La Jolla; Robin Thurmond, San Diego, all of CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 22 days.

(21) Appl. No.: 09/588,417

(22) Filed: Jun. 6, 2000

(51) Int. Cl.$^7$ .......................... C12Q 1/37; A61K 51/00; A61K 14/00
(52) U.S. Cl. ......................... 435/23; 424/169; 530/300
(58) Field of Search .................. 435/23, 69.2; 530/300

(56) References Cited

U.S. PATENT DOCUMENTS 5,859,253 A * 1/1999 Beckett et al. .............. 546/306

FOREIGN PATENT DOCUMENTS

WO  WO 97 35538  3/1997

OTHER PUBLICATIONS

Roberts C. et al, MDC–L, a novel metalloprotease disintegrin cysteine–rich protein family member expressed by human lymphocytes, J. Biol. Chem., 1999, 274, 29251–29259.*

Bohm, B.B., Aigner, T., Gehrsitz, A., Blobel, C.P., Kalden, J.R. and Burkhardt, H. (1999) Up–regulation of MDC15 (metargidin) messenger RNA in human osteoarthritic cartilage. *Arthritis Rheum.*, 42, 1946–1950.

Buroker–Kilgore, M. and Wang, K.K.W. (1993) A Coomassie Brilliant Blue G–250–based colorimetric assay for measuring activity of calpain and other proteases. *Anal. Biochem.*, 208, 387–92.

Coolican, S.A., Haiech, J. and Hathaway, D.R. (1986) The role of subunit autolysis in activation of smooth muscle Ca2+–dependent proteases. *J. Biol. Chem.*, 261, 4170–6.

Herren, B., Raines, E.W. and Ross, R. (1997) Expression of a disintegrin–like protein in cultured human vascular cells and in vivo. *Faseb J.*, 11, 173–180.

Howard, L., Nelson, K.K., Maciewicz, R.A. and Blobel, C.P. (1999) Interaction of the metalloprotease disintegrins MDC9 and MDC15 with two SH3 domain–containing proteins, endophilin I and SH3PX1. *J. Biol. Chem.*, 274, 31693–31699.

Kataoka, M., Yoshiyama, K., Matsuura, K., Hijiya, N., Higuchi, Y. and Yamamoto, S. (1997) Structure of the murine CD156 gene, characterization of its promoter, and chromosomal location. *J. Biol. Chem.*, 272, 18209–18215.

Lonergan, S.M., Johnson, M.H. and Calkins, C.R. (1995) Improved calpain assay using fluorescein isothiocyanate–labeled casein. *J. Food Sic.*, 60, 73–3, 78.

Nath, D., Slocombe, P.M., Stephens, P.E., Warn, A., Hutchinson, G.R., Yamada, K.M., Docherty, A.J.P. and Murphy, G. (1999) Interaction of metarfidin (ADAM–15) with avb3 and a5b1 integrins on different hemopoietic cells. *J. Cell Sci.*, 112, 579–587.

Ng, M. and Auld, D.S. (1989) A fluorescent oligopeptide energy transfer assay with broad applications for neutral proteases. *Anal. Biochem.*, 183, 50–6.

Roberts, c.M., Tani, P.H., Bridges, L.C., Laszik, Z. and bowditch, R.D. (1999) MDC–L, a novel metalloprotease disintegrin cysteine–rich protein family member expressed by human lymphocytes. *J. Biol. Chem.*, 274, 29251–29259.

Roghani, M., Becherer, J.D., Moss, M.L., Atherton, R.E., Erdjument–Bromage, H., Arribas, J., Blackburn, R.K., Weskamp, G., Tempst, P. and Blobel, C.P. (1999) Metalloprotease–disintegrin MDC9: intracellular maturation and catalytic activity. *J. Biol. Chem.*, 274, 3531–3540.

Sekut, L. and Connolly, K. (1998) AntiTNF–.alpha. agents in the treatment of inflammation. *Expert Opin. Invest. Drugs*, vol. 7, pp. 1825–1839.

Twining, S.S. (1984) Fluorescein isothiocyanate–labeled casein assay for proteolytic enzymes. *Anal. Biochem.*, 143, 30–4.

Wadstroem, T. and Smyth, C.J. (1973) Zymorgam methods applied to thin–layer isoelectric focusing in polyacrylamide gel. *Sci. Tools*, vol. 20, pp. 17–21.

Yamamoto, S., Higuchi, Y., Yoshiyama, K., Shimizu, E., Kataoka, M., Hijiya, N. and Matsuura, K. (1999) ADAM family proteins in the immune system. *Immunol. Today*, vol. 20, pp. 278–284.

Zhang, X.–P., Kamata, T., Yokoyama, K., Puzon–Mclaughlin, W. and Takada, Y. (1998) Specific interaction of the recombinant disintegrin–like domain of MDC–15 (metargidin, ADAM–15) with integrin avb3. *J. Biol. Chem.*, 273, 7345–7350.

\* cited by examiner

*Primary Examiner*—Nashaat T. Nashed
*Assistant Examiner*—Malgorzata Walicka
(74) *Attorney, Agent, or Firm*—John W. Wallen, III

(57) ABSTRACT

The present invention describes peptide substrates of the metalloproteases, ADAM8, ADAM15 and MDC-L. The invention also describes methods using these peptides to discover pharmaceutical agents that modulate these proteases. The invention further describes CD23 processing activity for these enzymes that may have important therapeutic implications for the use of inhibitors of these enzymes in allergic diseases such as asthma.

4 Claims, 10 Drawing Sheets

A. Full length ADAM protein

B. Recombinant soluble form

A.

B.

SEQUENCE LISTING

<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Lys Pro Ala Lys Phe Phe Arg Leu
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Lys Pro Ala Ala Phe Phe Arg Leu
 1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Arg Phe Ala Gln Ala Gln Gln Gln Leu Pro
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Pro Pro Val Ala Ala Ser Ser Leu Arg Asn
 1               5                  10

<210> SEQ ID NO 5
<211> LENGTH: 11
<212> TYPE: PRT
<213> ORGANISM: Artificial Sequence

```
<220> FEATURE:
<223> OTHER INFORMATION: Description of Artificial Sequence: synthetic
      peptide

<400> SEQUENCE: 5

Pro Ser Ala Ala Gln Thr Ala Arg Gln His Pro
  1               5                  10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Arg Pro Leu Gly Leu Ala Arg
  1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Arg Val Arg Arg Ala Leu Pro Ser
  1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Pro Leu Ala Gln Ala Val Arg Ser Ser Ser
  1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Arg Gly Val Val Asn Ala Ser Ser Arg Leu Ala Lys
  1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Leu Ala Gln Ala Val Arg Ser Ser Ser Arg
  1               5                  10
```

-continued

```
<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Arg Thr Ala Ala Val Phe Arg Pro
 1               5
```

METALLOPROTEASE PEPTIDE SUBSTRATES AND METHODS

FIELD OF THE INVENTION

The present invention describes peptide substrates of the metalloproteases ADAM8, ADAM15 and MDC-L. The invention also describes methods using these peptides to discover pharmaceutical agents that modulate these proteases. The invention further describes CD23 processing activity for these enzymes that may have important therapeutic implications for the use of inhibitors of these enzymes in allergic diseases such as asthma.

BACKGROUND OF THE INVENTION

The disintegrin metalloprotease (or ADAM) family of cell surface proteolytic enzymes is known to play roles in sperm-egg binding and fusion, muscle cell fusion, neurogenesis, modulation of Notch receptor and ligand processing, and processing of the pro-inflammatory cytokine, TNFα. The TNFα-converting enzyme, TACE or ADAM17, is currently a target for anti-inflammatory drugs (McGeehan et al., 1997; Sekut and Connolly, 1998), and other members of this family are likely to be good therapeutic targets. The genes for ADAM8, ADAM15 and MDC-L have been cloned and shown to contain the consensus sequence for an active metalloprotease, but their in vivo substrates are unknown. No proteolytic activity has been demonstrated for these proteins, apart from one reference to unpublished observations that murine ADAM8 expressed in yeast cells showed MMP-3-like, substance P degrading activity (K. Matsuura, unpublished, reported in (Yamamoto et al., 1999).

ADAM8 has been reported to be expressed almost exclusively in cells of the immune system, particularly B-cells, monocytes and granulocytes. Furthermore, its expression has been shown to be inducible by LPS and γ-interferon (Kataoka et al., 1997). ADAM8 is specifically expressed in eosinophils, one of the most important effector cell types at the site of inflammation in allergic asthma. ADAM8 therefore represents a therapeutic target for human diseases, such as for the treatment of allergy and/or asthma.

ADAM15 is a membrane-bound disintegrin metalloprotease containing an RGD integrin-binding sequence, which may function in cell adhesion through binding to integrin αvβ3 (Nath et al., 1999; Zhang et al., 1998), and two proline-rich sequences, shown to interact with SH3 domains in endophilin-I and SH3PX1 (Howard et al., 1999). ADAM15 is found in human aortic smooth muscle and cultured umbilical vein endothelial cells. While ADAM15 is not expressed in normal blood vessels, it has been detected in developing atherosclerotic lesions (Herren et al., 1997), and has also been shown to be upregulated in osteoarthritic versus normal human cartilage (Bohm et al., 1999). Thus ADAM15 plays a role in the atherosclerosis and/or cartilage degeneration. ASAM15 therefore represents a therapeutic target for human diseases, such as for the treatment of osteoarthritis and atherosclerosis.

A member of the ADAM family, MDC-L, was recently cloned and shown to be specifically expressed by lymphocytes in two alternative forms, a membrane-bound form, MDC-Lm, and a secreted protein, MDC-Ls (Roberts et al., 1999). The lymphocyte-specific expression of MDC-L suggests that it may have an important immunological function, but its in vivo substrate(s) are unknown and proteolytic activity has not been previously demonstrated.

Excessive production of IgE is believed to be a major mediator of allergic responses(Corry and Kheradmand, 1999), resulting in pathophysiology ranging from inflammation to severe bronchoconstriction. IgE binds to two different receptors, the high affinity IgE receptor found on mast cells and basophils, and CD23, the low affinity IgE receptor, expressed on the surface of B cells (Corominas et al., 1993), monocytes(Alderson et al., 1992), macrophages (Melewicz et al., 1982), and eosinophils(Sano et al., 1999). The latter receptor, CD23, is subject to proteolytic release of soluble extracellular fragments (Letellier et al., 1989), which have been shown to cause upregulation of IgE production (Aubry et al., 1992; Yu et al., 1994)and induction of inflammatory cytokines(Armant et al., 1994; Armant et al., 1995). Increased levels of soluble CD23 have been observed in allergic asthma (Di Lorenzo et al., 1999; Monteseirin et al., ; Yanagihara et al., ), in chronic B-lymphocytic leukemia (Beguin et al., ; Dine et al., ; Knauf et al., 1997) and in rheumatoid arthritis(Bansal et al., 1994; Chomarat et al., 1993; Ribbens et al., 2000).

The implication of soluble CD23 in the upregulation of IgE production suggests that inhibition of the enzyme(s) responsible for CD23 processing may offer a therapeutic approach for the treatment of allergic diseases. In support of this theory, it has been shown that inhibition of CD23 proteolysis can significantly inhibit IgE release in B cell lines (Christie et al., 1997; Wheeler et al., 1998), and in mouse models of IgE production and bronchoconstriction in response to ovalbumin challenge (Christie et al., 1997; Dasic et al., 1999).

The production of soluble CD23 is mediated by a membrane-bound metalloprotease (Marolewski et al., 1998), which can be inhibited by compounds that do not affect matrix metalloprotease activity(Bailey et al., 1998; Bailey et al., 1999). The prior art does not identify the specific metalloprotease that cleaves CD23 to generate the upregulation of allergic response, thus this remains an unmet need in the development of therapeutics to treat human immune diseases such as allergy.

SUMMARY OF THE INVENTION

The present invention describes peptide substrates of the metalloproteases ADAM8, ADAM15 and MDC-L, represented by the peptides in Table 1. The peptides of the present invention are useful in assays to identify modulators of the activity of ADAM8, ADAM15 and MDC-L, particularly those compounds that inhibit ADAM8, ADAM15 and MDC-L enzymatic activity.

The present invention also demonstrates that ADAM8, which is found on the same cell types as CD23, is able to process membrane-bound CD23 on human macrophage and B cell lines. Thus the present invention provides methods to measure the decrease of cell-surface CD23 or increase of soluble fragments of CD23 produced by the enzymatic activity of ADAM8, ADAM15, or MDC-L. Further the present invention provides assays to test putative modulators of ADAM8, ADAM15, or MDC-L enzymatic activity towards CD23.

DETAILED DESCRIPTION OF THE INVENTION

Figure 1:
FIG. 1 Domain structures of (A) full-length ADAM proteins and (B) the recombinant soluble forms used in the protease assays.
Figure 1:

Soluble forms of human ADAM8, ADAM15 and MDC-L, consisting of the pro- and protease domains, were produced and purified by affinity chromatography in inactive precursor forms. Upon storage at 4° C. an auto-activation process, including removal of the pro- domain, occurs, thus yielding active enzyme. By screening a collection of 49 potential peptide substrates, nine different peptide sequences were found that were cleaved with significant activity by ADAM8, ADAM15 and MDC-L. Seven out of these nine peptides were not cleaved by ADAM17/TACE. The relative affinities and specific cleavage sites for ADAM8 within the respective peptides were determined for four of these peptides. The peptide with the highest relative affinity was used to optimize the assay in a format suitable for high throughput screening, which will enable identification of modulators,; such as small molecule modulators, of ADAM8, ADAM15 and MDC-L activity as potential therapeutic compounds.

The present invention provides peptide substrates useful to measure the enzymatic activity of ADAM8, ADAM15 and MDC-L metalloproteases. The amino acid sequence of these peptides is provided in single letter code in Table 1. Some peptides are better substrates for some ADAM proteins than others, and are designated by a ranking system from one star (*) to five stars (*****) to indicate weaker to more potent substrates respectively.

TABLE 1

Relative activities of ADAM8, ADAM15, MDC-L and ADAM17 for 11 different FRET peptides

| | Peptide | | Relative proteolytic activity | | | |
|---|---|---|---|---|---|---|
| SEQ. ID | name | peptide sequence | ADAM8 | ADAM15 | MDC-L | ADAM17 |
| 1 | CatEl | X-KPAKFFRL-Z | ***** | ***** | ***** | (—) |
| 2 | CatE | X-KPAAFFRL-Z | ***** | ***** | ***** | (—) |
| 3 | CD27L | X-RFAQAQQQLP-Z | **** | **** | **** | (—) |
| 4 | KL1 | X-PPVAASSLRN-Z | *** | *** | *** | (—) |
| 5 | TNFB2 | X-PSAAQTARQHP-Z | *** | *** | *** | (—) |
| 6 | Mat | Z-RPLGLAR-X | *** | *** | *** | *** |
| 7 | AD8P2 | X-RVRRALPS-Z | *** | *** | *** | (—) |
| 8 | TNFα | X-PLAQAVRSSS-Z | *** | *** | *** | *** |
| 9 | KAS-1 | Z-RGVVNASSRLAK-X | *** | *** | *** | (—) |
| 10 | TNFα(-4 + 6) | Z-LAQAVRSSSR-X | * | * | * | *** |
| 11 | AD8P | X-RTAAVFRP-Z | * | * | * | ***** |

(X = Edans-E; Z = dabcyl-K; (—) = no detectable activity)

The peptides of the present invention are useful in assays for modulators of the activity of ADAM8, ADAM15 and MDC-L, particularly those compounds that inhibit their enzymatic activity. The term "peptides" refers to natural or synthetic amino acids linked by a peptide bond. The peptide sequence may be a portion of a larger polypeptide or protein, or may be as small as the sequences listed in Table 1. One embodiment of the present invention provides a homogeneous in vitro protein-based assay to detect compound modulation of ADAM8, ADAM15 and MDC-L enzymatic activity. Homogeneous refers to an assay conducted in a single vessel without manipulation after the reaction is set up. In one embodiment of the method of the present invention, the method comprises the steps;

1) combining a compound, ADAM8, ADAM15 or MDC-L enzyme protein, and peptide substrate,
2) incubating the compound, enzyme, and substrate for sufficient time to produce a detectable product as a result of enzymatic activity upon the substrate; and
3) measuring a change in the quantity of product as a result of compound modulation of expected ADAM8, ADAM15 or MDC-L enzymatic function.

A wide variety of variation in the methods described generally abode are readily apparent to one of ordinary skill in the art, and would be suitable for the method of the present invention.

Functional enzyme protein refers to protein that is capable of enzymatic cleavage of a peptide substrate.

The term "compound" as used herein in connection with a modulator of a enzymatic activity refers to an organic molecule that has the potential to modulate the specific enzymatic activity of the enzyme. For example, but not to limit the scope of the present invention, compounds may include, but are not limited to, small organics, synthetic or natural amino acid peptides, proteins, or synthetic or natural nucleic acid sequences, or any chemical derivatives of the aforementioned. The term "chemical derivative" describes a molecule that contains additional chemical moieties that are not a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

The methods described herein are especially useful for high throughput screening of compounds with the purpose to identify compounds that modulate metalloprotease function. The term "high throughput" refers to an assay design that allows easy analysis of multiple samples simultaneously, and capacity for robotic manipulation. Preferred assays are homogeneous assays. Another desired feature of high throughput assays is an assay design that is optimized to reduce reagent usage in order to achieve the analysis desired. The methods described herein demonstrate highly robust performance, and good linearity as a function of enzyme concentration and substrate concentration. At appropriately adjusted enzyme and substrate concentrations, the assay was linear for up to approximately two hours. From FIG. 6A, it can be seen that for kinetic analysis, the signal-to-noise ratio is effectively infinite, as no change in the background (blank, no enzyme) is observed over the time of the assay. For endpoint measurements, the enzyme and substrate concentrations could be adjusted to achieve the desired signal-to-noise ratio. In the example in FIG. 6A, it can be seen that this ratio (control versus blank endpoints) was approximately ten. Therefore the amount of reagent used can be varied to utilize a minimum of certain reagents, such as a recombinant enzyme or test compound. Examples of assay formats include, but are not limited to, 96-well or 384-well plates, levitating droplets, and "lab on a chip" microchannel chips used for liquid handling experiments. A device suitable for producing levatating droplets is described in International patent application WO 9944746 entitled "SYSTEM FOR PERFORMING ASSAYS ON A LEVITATED DROPLET" by Laurell et al and published on Sep. 10, 1999. Microchannel chips are well known in the art, and can be practiced using the methods described, for example, in U.S. Pat. No. 6,001,229 by Ramsey and issued on Dec. 14, 1999. It is well known by those of ordinary skill in the art that as miniaturization of plastic molds and liquid handling devices are advanced, or as improved assay devices are designed, that greater numbers of samples may be performed using the methods of the present invention.

In another embodiment, the present invention also provides a homogeneous in vitro. cell-based method to detect compound modulation of ADAM8, ADAM15 and MDC-L enzymatic activity. One embodiment of such a method comprises the steps;

1) combining a test compound, functional enzyme on the surface of a cell, and a peptide substrate,
2). incubating the compound, cell-bound enzyme, and substrate for sufficient time to produce a detectable product as a result of enzymatic activity upon the substrate; and
3) measuring a change in the quantity of product as a result of compound modulation of expected ADAM8, ADAM15 or MDC-L enzymatic function.

Alternatively, as is readily apparent to one of ordinary skill in the art, the assays described above could be made non-homogeneous. One embodiment of such an assay would be by way of immobilizing the substrate peptide, for instance by use of an affinity moiety—affinity capture pair such as streptavidin capture of a biotinylated substrate peptide. Affinity capture pairs are well known in the art and include, for example, avidin/biotin, antibody capture of a region of the substrate peptide, and polyhistidine/immobilized nickel. An embodiment of such a non-homogeneous method of the present invention comprises the steps, in order:

1) combining a substrate peptide comprising an affinity moiety, an ADAM8, ADAM15 or MDC-L cleavage site, and a detectable label, said affinity moiety and label located on opposite sides of the cleavage site;
2) contacting the substrate peptide with an affinity capture coated solid phase support for sufficient time to bind a portion of the peptide;
3) washing the support to remove unbound peptide;
4) contacting a solution comprising a test compound and functional ADAM8, ADAM15 or MDC-L enzyme with the peptide bound solid phase support for sufficient time to allow enzymatic cleavage of the substrate, thereby releasing the substrate and detectable label into the solution;
5) transferring the solution to a vessel; and
6) measuring changes in the quantity of the detectable label as a result of compound modulation of expected ADAM8, ADAM15 or MDC-L enzymatic function.

The change in the quantity of product can be expressed as the total amount of product produced as a function of time (a stop-time assay) or can be kinetic by measuring a change in the enzymatic rate as a function of time. Kinetic assays are measured from the time of initial contact of the enzyme and substrate to a point in time where approximately 50% of the maximum observed product is generated.

The amount of expected ADAM8, ADAM15 or MDC-L enzymatic activity can be determined by running, concurrently or separately, an assay as herein described with a compound that does not inhibit enzymatic activity, or with a solvent vehicle that contains similar properties as that used for the test compound but lacks any test compound, such as DMSO, DMF, or isopropyl alcohol.

The amount of time necessary for contact with the compound is determined, for example, by running a time course with a known ADAM8, ADAM15 or MDC-L modulator and measuring changes as a function of time.

The assay methods of the present invention may also utilize cells or cell extracts or purified fractions as a source of enzyme. Cells useful in the cell-based enzyme assay of the present invention are those cells such as from the immune system, and other sources, that express the on their cell surface or secrete the enzyme. Reagents well known in the art such as fluorescently labelled antibodies, are used to determine the presence of ADAM8 on the cell surface by methods that are standard and well known in the art. Preferred cell types for use in the cell-based method described herein include macrophage, macrophage-derived lineage, monocytes, and granulocytes. In addition, cells transfected with recombinant ADAM8 that express ADAM8 protein are useful as a source of enzyme. These cells may be cell lines or primary cells from any mammal, preferably murine, rat, rabbit, monkey, chimpanzee, or human. Cells expressing other metalloproteases, including but not limited to ADAM15 and MDC-L can be identified, for example, by using the cell based methods described for ADAM8 herein, or can be produced recombinantly by transfecting DNA encoding the desired enzyme into a cell as described for ADAM8.

Methods for detecting compounds that modulate ADAM8 proteolytic activity comprise combining a putative modulating compound, functional enzyme protein, and a suitable labeled substrate and monitoring an effect of the compound on the protease by changes in the amount of substrate or product either as a function of time or after a predefined period of time. Labeled substrates include, but are not limited to; substrate that is radiolabeled (Coolican et al., 1986), fluorometric (Lonergan et al., 1995; Twining, 1984) or colorimetric (Buroker-Kilgore and Wang, 1993). Radioisotopes useful in the present invention include those well known in the art, including $^{125}$I, $^{131}$I, $^{3}$H, $^{14}$C, $^{35}$S, $^{32}$P, and $^{33}$P. Radioisotopes are introduced into the peptide by conventional means, known to those skilled in the art, such as iodination of a tyrosine residue, phosphorylation of a serine or threonine residue, or incorporation of tritium, carbon or sulfur utilizing radioactive amino acid precursors. Zymography following SDS polyacrylamide gel electrophoresis (Wadstroem and Smyth, 1973) as well as by fluorescent resonance energy transfer (FRET)-based methods (Ng and Auld, 1989) are also methods measure enzymatic activity, and thereby identify ADAM8 enzymatic activity. Compounds that are agonists will increase the rate of substrate degradation and will result in less remaining substrate or more product as a function of time. Compounds that are antagonists will decrease the rate of substrate degradation and will result in greater remaining substrate or less product as a function of time.

One preferred assay format useful for the method of the present invention is a FRET based method using peptide substrates that contain a fluorescent donor with either a quencher or acceptor that are separated by a peptide sequence encoding the cleavage site within the substrate for the enzyme. A fluorescent donor is a fluorogenic compound that can absorb energy and transfers a portion of the energy to another compound. Examples of fluorescent donors suitable for use in the present invention include, but are not limited to, coumarins, xanthene dyes such as fluoresceines, rhodols, and rhodamines, resorufins, cyanine dyes bimanes, acridines, isoindols, dansyl dyes, aminophthalic hydrazides such as luminol and isoluminol derivatices, aminophthalimides, aminonapthalimides, aminobenzofurans, aminoquinolines, dicanohydroquinones, and europium and terbium complexes and related compounds. A quencher is a compound that reduces the emission from the fluorescent donor when it is appropriately proximally located to the donor, and do not generally re-emit the energy in the form of fluorescence. Examples of such moieties include indigos, bezoquinones, anthraquinones, azo compounds, nitro compounds, indoanilines, and di- and triphenylmethanes. A FRET method using a donor/quencher pair measures increased emission from the fluorescent donor as a function of enzymatic activity upon the peptide substrate. Therefore a test compound that antagonizes enzymatic activity will generate an emission signal intensity that is between two control samples—a low (basal) fluorescence from the FRET peptide alone and a higher fluorescence from the FRET peptide digested by the activity of the enzyme. An acceptor is a fluorescent molecule that absorbs energy from the fluorescent donor and re-emits a portion of the energy as fluorescence. An acceptor is a specific type of quencher that enables a separate mechanism to measure proteolytic efficacy. Methods that utilize a donor/acceptor pair measure a decrease in acceptor emission as a function of enzymatic activity upon the peptide substrate. Therefore a test compound that antagonizes the enzymatic activity of the enzyme will generate an emission signal between two control samples—a higher basal fluorescence from the FRET peptide alone and a lower fluorescence from the FRET peptide digested by the enzymatic activity of enzyme. Examples of acceptor molecules useful for methods of the present invention include, but are not limited to, coumarins, fluoresceins, rhodols, rhodamines, resorufins, cyanines, difuoroboradiazindacenes, and phthalcyanines.

It is readily apparent to those of ordinary skill in the art that the mehtods of the present invention are suitable for use with a variety of metalloproteinases. In addition, it is readily apparent to those skilled in the art that a variety of metalloproteinases, including but not limited to ADAM8, ADAM15, and MDC-L, are suitable for use in any particular embodiment of the method of the present invention.

The present invention also provides a method for measuring ADAM8, ADAM15-, or MDC-L- mediated cleavage of membrane-bound CD23 from the surface of cultured macrophage, monocyte, eosinophilic or B cell lines, and an example is provided for measuring the effect of an inhibitory compound on this process. Cleavage of membrane-bound CD23 could be measured by monitoring the decrease in the membrane-bound form (by flow cytometry of cells or Western blotting of cell extracts) or by monitoring the increase in soluble forms of CD23 (by ELISA or Western blotting of the medium from cells, in the absence or presence of appropriate inhibitors). Preferred cell lines expressing CD23 on their cell surface include U937 macrophage line, THP-1 monocytic line, EoL1 eosinophilic leukemia cell line, JY and Raji B cell lines, and the lymphoblastoid B cell line, 8.1.6.

The following examples illustrate the present invention without, however, limiting the same thereto.

EXAMPLE 1

GENERATION OF SOLUBLE RECOMBINANT ENZYME

ADAM proteins usually comprise: an N-terminal pro-domain and a metalloprotease domain, followed by the disintegrin domain, cysteine-rich domain, epidermal growth factor repeat, transmembrane domain and cytoplasmic tail, as illustrated in FIG. 1. For production of biologically active and soluble ADAM proteins (ADAM8, ADAM15 and MDC-L), PCR products containing the pro- and protease domains and a C-terminal FLAG epitope (used for immunodetection and purification) were cloned into pFastBac1 (GibcoBRL) and pcDNA3 (Invitrogen) vectors using standard techniques.

Figure 2:
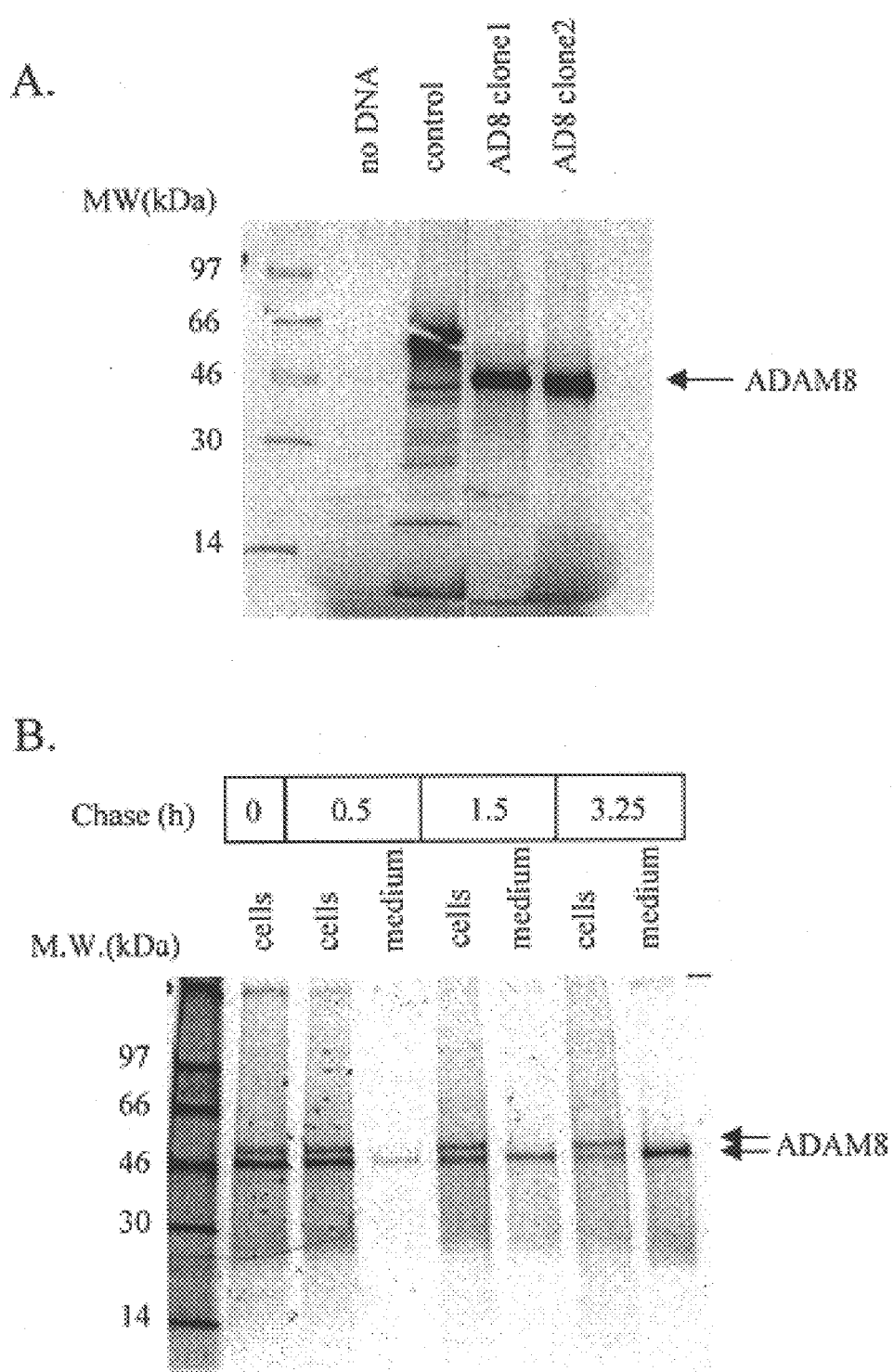
FIG. 2 Expression of recombinant ADAM8 in vitro and in mammalian cells (A) In vitro translation of soluble ADAM8
(B) Pulse-chase analysis of recombinant soluble ADAM8 expression and secretion in COS7 cells FIG. 3 Expression of recombinant soluble ADAM8 by Sf9 insect cells and purification from the medium
(A) Gelcode® Blue stain
(B) M2-anti-FLAG Western blot to detect ADAM8

To confirm correct cloning, soluble human ADAM8, containing the pro- and protease domains, was translated in vitro from the cDNA cloned into pcDNA3 using T7 polymerase. The reactions were performed in the presence of $^{35}$S-methionine using the Promega TNT kit according to the manufacturer's instructions. Reaction products were analyzed by SDS-PAGE (4–20%) and fluorography. As shown in FIG. 2A, the translated protein migrated to the expected molecular weight. The cDNA constructs were then used to transfect COS7 cells using Superfect (Quiagen) as recommended by the manufacturer. Three days after transfection, cells were labelled for 30 minutes at 37° C. with $^{35}$S-methionine (100 μCi per ml) followed by chase times of 0.5 to 3.25 hours. At each time point, the medium was collected and the cells were lysed in PBS containing 1% NP-40 and Complete protease inhibitors (Boehringer Mannheim). Immunoprecipitation was performed on both media and cell lysates using the M2-αFlag-agarose. The immunoprecipitates were subjected to SDS-PAGE (5–15% acrylamide) and fluorography. As shown in FIG. 2B, the secretion of soluble ADAM8 into the medium can be detected as early as 0.5 hours, increasing up to 3.25 hours, thus confirming that the recombinant proteins were not membrane bound or retained intracellularly.

In order to generate large quantities of protein for biological testing and assay development, Sf9 cells were infected with pFastBac (GibcoBRL) containing the soluble ADAM protein constructs of ADAM8, ADAM15, and MDC-L, described above.

Figure 3:
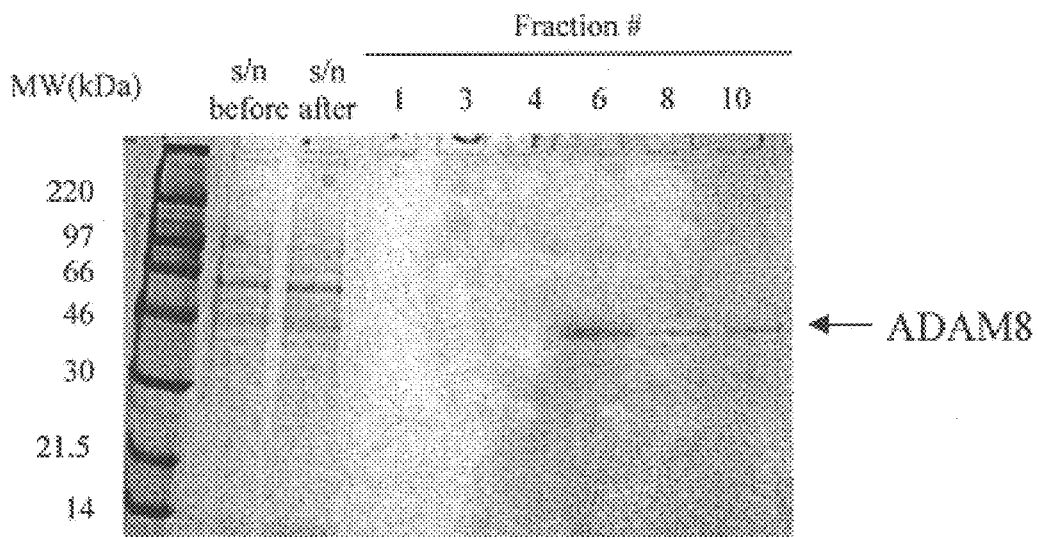
Figure 3:
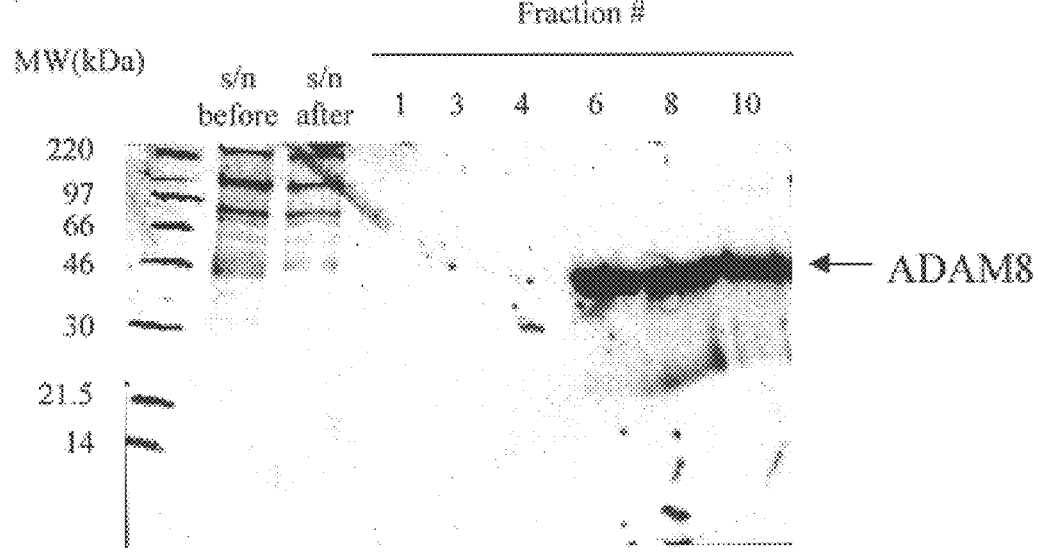

Recombinant baculovirus for soluble ADAM8 expression was generated from the pFastBac1 construct described above using the Bac-to-Bac system (Gibco BRL). Sf9 cells were infected with baculovirus and the medium was collected after 72 hours. The medium was concentrated 10-fold by ultrafiltration, and exchanged to TBS (Tris Buffered Saline) by repeated addition and re-concentration. The supernatant was centrifuged for one hour at 15000×g, filtered through a 0.45 uM filter to remove debris, and incubated, with mixing, overnight at 4° C. with M2-αFlag-agarose. The resin was loaded into a column and washed with TBS, followed by elution of the bound material with 0.1M Glycine (pH 3.5) and immediate neutralization by addition of 12.5 ul/ml of 2M Tris-HCl, pH 8. The supernatant from the infection (before and after incubation with M2-αFlag-agarose) and fractions from the purification were analyzed by SDS-PAGE followed by staining (FIG. 3A) and Western blotting (FIG. 3B). FIG. 3A shows fractions containing the immunopurified ADAM8 protein, and FIG. 3B, the M2αFlag antibody detection of a band at the expected molecular weight. This protein was then used to test potential substrate peptides.

An analogous process was conducted with ADAM17, ADAM15 and MDC-L in order to generate sufficient quantities of protein for subsequent peptide substrate screening.

EXAMPLE 2

FRET ASSAY: PEPTIDE SUBSTRATE SCREENING

Forty nine different peptides were synthesized for testing protease activity. The peptides comprised (i) a collection of substrates for other proteases, as well as (ii) a number of sequences corresponding to membrane proximal cleavage sites of various proteins postulated to be released by metalloproteases (including those published by (Roghani et al., 1999) for ADAM9/MDC9). In order to use the principle of fluorescence resonance energy transfer, or FRET, for the assay, the peptides were labelled at the C-terminus with Dabcyl and at the N-terminus with Edans. Thus cleavage of the peptides can be monitored by the increase in Edans fluorescence at 460 nm (excitation 360 nm) as a result of the decrease in proximity of the Dabcyl quencher. The assay was performed by diluting the ADAM8, ADAM15, MDC-L, or ADAM17 (50 to 100 ng of protein, one to two picomoles) in assay buffer, 10 mM HEPES, pH 7.5, containing 0.001% Brij35. The reaction was initiated by the addition of peptide substrate to a final concentration of 20 uM. The assays were typically run for 20 to 60 minutes at room temperature and the slope of the kinetic increase in fluorescence was determined to calculate the rate of the reaction. If necessary, it was possible to stop the reaction at a certain time by the addition of $\frac{1}{10}^{th}$ volume of 1M NaOAc (sodium acetate), pH 3.5.

Figure 4:
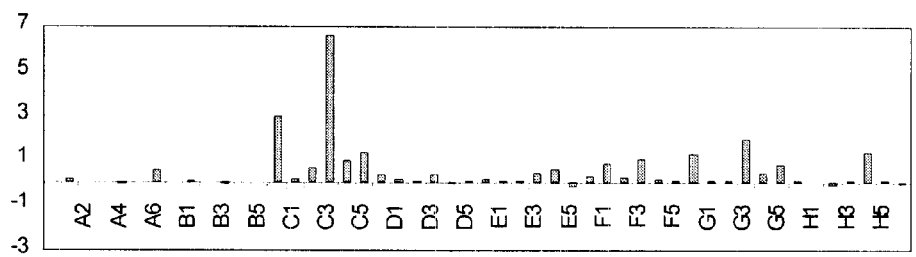
FIG. 4 Relative activities of ADAM8, ADAM15, MDC-L and ADAM17 for 49 different FRET peptides (numbered A1 to H6)
Figure 4:
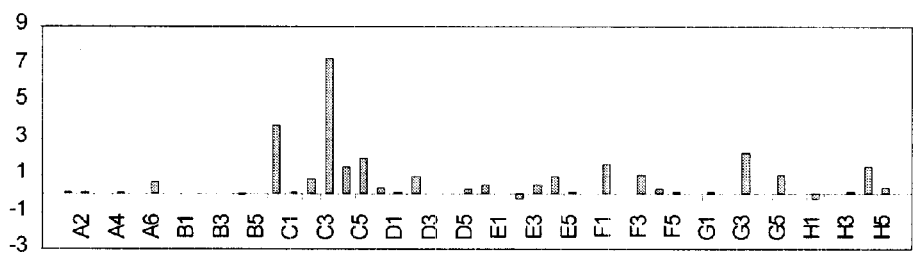
Figure 4:
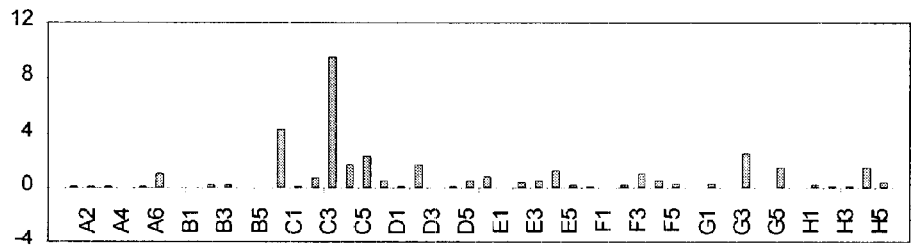
Figure 4:
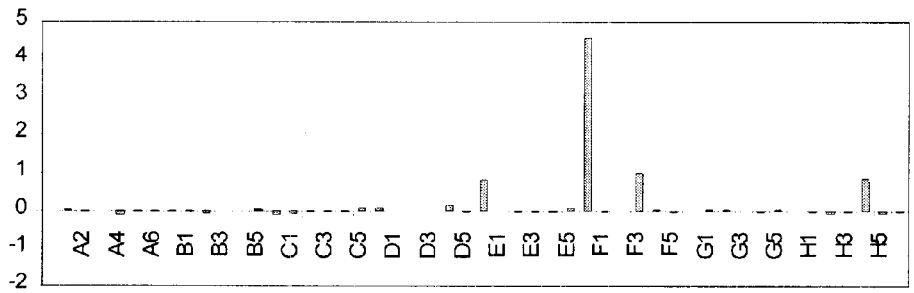

FIG. 4 shows the relative activities for the different peptides (numbered A1 to H6) expressed in arbitrary units, normalized by setting the activity for peptide F3 to one unit. This peptide was cleaved by all enzymes, and thus was chosen to represent a standard by which to compare the relative activity of the various enzymes for their potential to cleave the various peptide substrates. While ADAM8, ADAM15 and MDC-L showed a very similar activity profile for the various peptides, ADAM17 appeared to have a significantly different specificity and was able to cleave fewer of the peptides than the other three proteases.

Kinetic Analysis of the Affinity of ADAM8 for Cleavage of 4 Different Peptides

Figure 5:
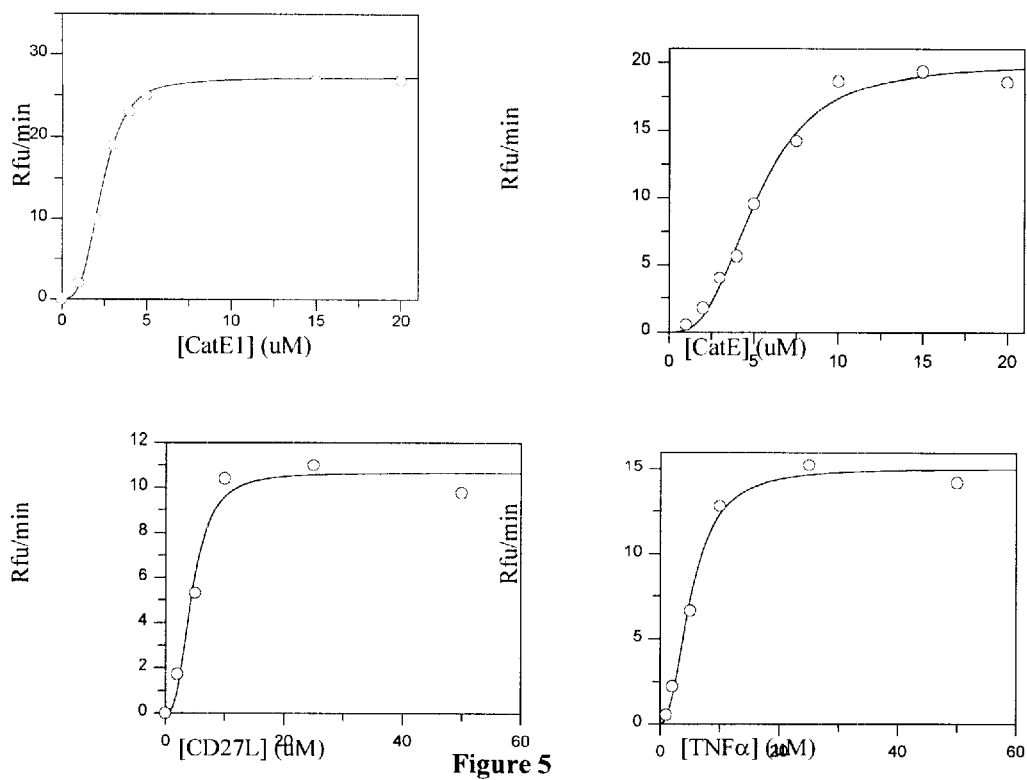
FIG. 5 Kinetic analysis of the relative affinities of ADAM8 for cleavage of 4 different peptides FIG. 6 Use of the ADAM8 peptide cleavage assay to look for inhibitory compounds (A) Comparison of inhibition of ADAM8 proteolytic activity by compounds A, B and C;
(B) IC50 analysis for inhibition of ADAM8 by Inhibitor C FIG. 7 FRET peptide zymography of inactive versus active ADAM8

To confirm the screening assay, ADAM8 was further analyzed for its catalytic rate for 4 different peptides. The assay was performed by diluting the ADAM8 in assay buffer, 10 mM HEPES, pH 7.5, containing 0.001% Brij35. The reaction was initiated by the addition of substrate to different final concentrations, as indicated in FIG. 5, for analysis of affinities. The assay was run for 30 minutes at room temperature. FIG. 5 shows the proteolytic activity (in relative fluorescence units per minute) as a function of peptide concentration for CatE1, CatE, CD27L, and TNFα. The curves were fitted to the data with the program Grafit (Erithacus Software). The data showed allosteric kinetics with a Hill coefficient of approximately 3, implying the equivalent of three co-operative active sites. The results of these analyses are provided in Table 2. The Vmax for each substrate was calculated by non-linear fitting of the data. The substrate concentration at which the enzyme activity was 50% of the Vmax (designated "$K_{0.5}$") was determined by inspection of the fitted curves. Table 2 also provides the cleavage site of ADAM8 within each peptide, as indicated by a carot within the peptide sequence.

TABLE 2

$K_{0.5}$ of ADAM8 for peptides

| PEPTIDE | CLEAVAGE SITE | $K_{0.5}$ |
|---------|---------------|-----------|
| CatE1   | XKPAKF^FRLZ   | 2.5 uM    |
| CatE    | XKPAAF^FRLZ   | 5 uM      |
| CD27L   | XRFAQA^QQQLPZ | 5 uM      |
| TNFα    | XPLAQAVRS^SSZ | 5 uM      |

EXAMPLE 3

DRUG SCREENING ASSAY

ADAM8 (50 to 100 ng of protein, one to two picomoles) was diluted in assay buffer, 10 mM HEPES, pH 7.5, containing 0.001% Brij35. Then samples were prepared containing putative inhibitors A, B, and C (dissolved in 10% DMSO) at a final concentration of 10 micromolar. The final %DMSO in the assay was 1% and it was determined experimentally that up to 3% final DMSO was not detrimental to the activity of the enzyme. The reaction was initiated by the addition of peptide substrate to a final concentration of 20 uM and readings were taken at one minute intervals, for a total of 30 minutes at room temperature.

The assay was always performed at enzyme and substrate concentrations where the activity was linearly related to enzyme concentration, and where the increase in fluorescence (reaction rate) was linear for at least the time of the assay. At appropriately adjusted enzyme and substrate concentrations, the assay was linear for up to two hours. From FIG. 6A, it can be seen that for kinetic analysis, the signal-to-noise ratio is effectively infinite, as no change in the background (blank, no enzyme) is observed over the time of the assay. For endpoint measurements, the enzyme and substrate concentrations could be adjusted to achieve the desired signal-to-noise ratio. In the example in FIG. 6A, it can be seen that this ratio (control versus blank endpoints) was approximately ten.

Figure 6:
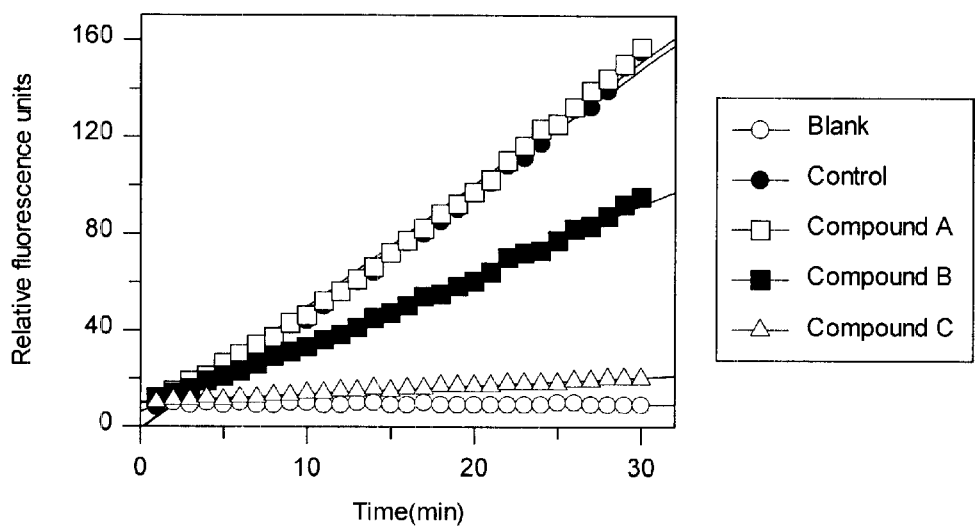
Figure 6:
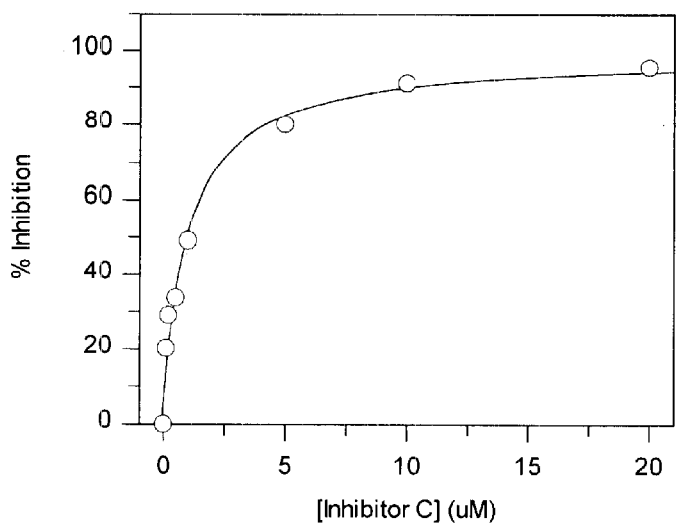
Figure 7:
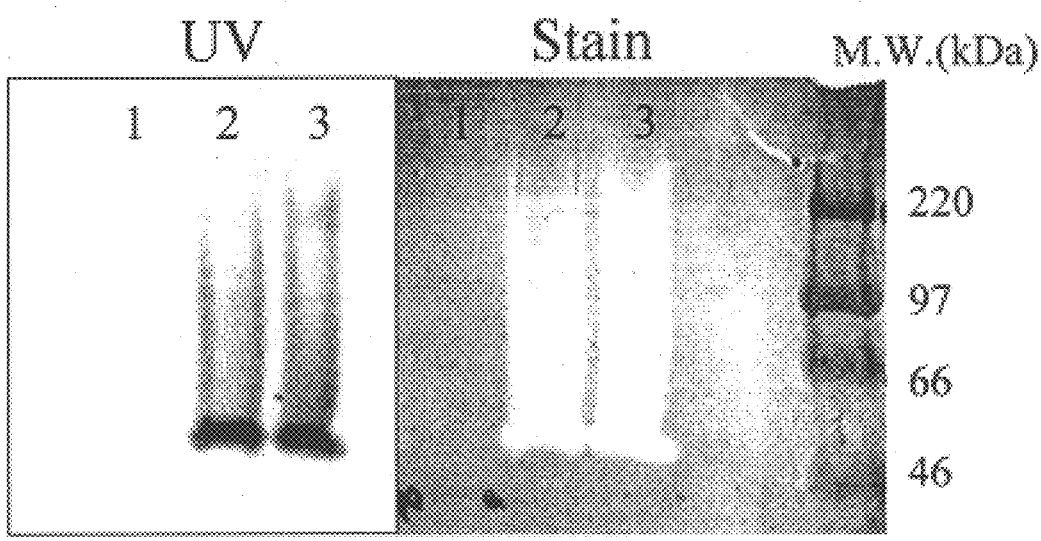

FIG. 6A shows that inhibitor C completely abolished enzyme activity (results are comparable to blank [no enzyme]), inhibitor B showed some inhibition of the ADAM8 enzyme, while inhibitor A is inactive against ADAM8 (results are comparable to control [no inhibitor]).

IC50 Analysis for Inhibition of ADAM8 by Inhibitor C

ADAM8 (50 to 100 ng of protein, one to two picomoles) was diluted in assay buffer, 10 mM HEPES, pH 7.5, containing 0.001% Brij35. Samples were prepared containing Inhibitor C at final concentrations ranging from 0.1 to 20 uM (final DMSO concentration of 3%). Duplicate assays were run for each concentration of Inhibitor C for 30 minutes at room temperature. The reaction rates in the absence (control) and presence of various Inhibitor C concentrations were determined by linear regression. of the data, and the percent inhibition relative to the control reaction rate was calculated. The data in FIG. 6B were fitted by non-linear regression to a single-site saturation curve using the program Grafit (Erithacus Software). The IC50 for inhibition of ADAM8 by Inhibitor C, calculated from the non-linear fit, was 1±0.3 uM. The IC50 was also calculated (using Grafit) by fitting the rate data to a 3-parameter equation where the lower data limit is corrected to zero, and this analysis method also yielded a similar IC50 of 1±0.2 uM.

EXAMPLE 4

FRET PEPTIDE ZYMOGRAPHY OF INACTIVE VERSUS ACTIVE ADAM8

Samples for zymography were dissolved in sample buffer without reducing agent, at a final SDS concentration of 2%. Samples were loaded on 7.5% or 10% PAGE gels and run in SDS electrophoresis buffer at 4° C. (Laemmli). Once the run was complete, the gels were soaked while shaking for 2×15 min in 50mM Tris pH 7.5, 10 uM $ZnCl_2$ and 2.5% TritonX-100 to replace the SDS. The gel was then rinsed for 2×5 min in the same buffer without TritonX-100. The gel was then soaked in assay buffer containing 100 uM CatE1 FRET peptide, identical to that used for the proteolytic activity assay described above. Active proteolytic species could then be visualized under UV light, or by "negative" staining with Gelcodeo® Blue following rinses in water to remove excess peptide. Lane 1 contains a sample of ADAM8 containing the inhibitory pro-sequence, and which showed no activity in the fluorometric proteolytic assay described above, and lanes 2 and 3 contain active, processed, ADAM8 preparations.

EXAMPLE 5

PRODUCTION OF ANTIBODIES AGAINST ADAM8 AND ADAM15

Figure 8:
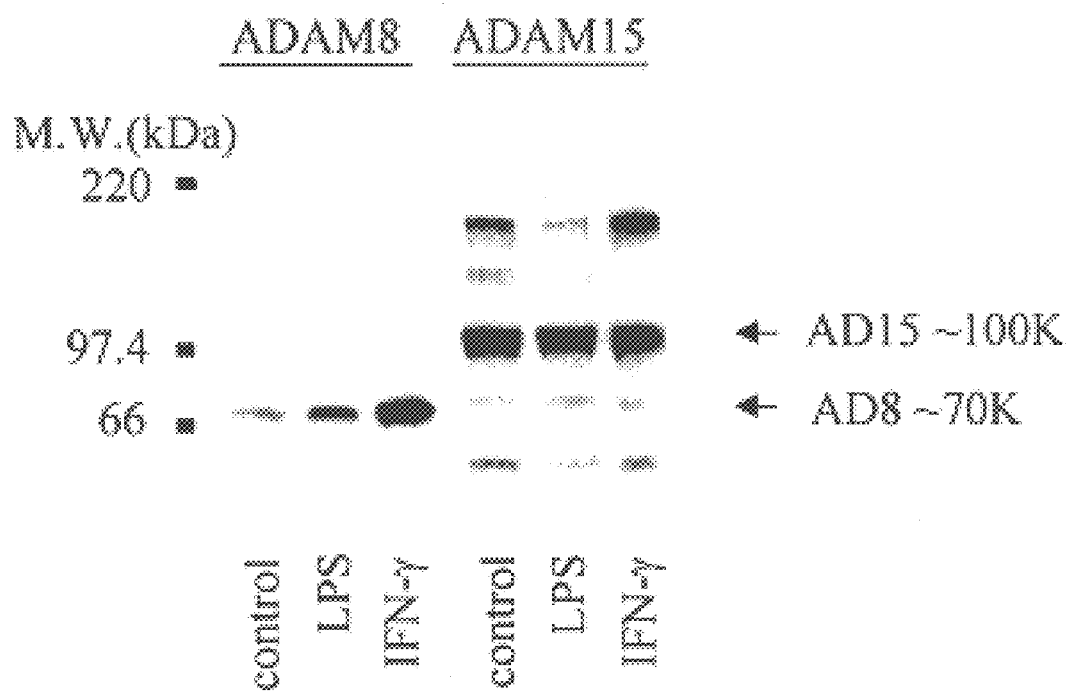
FIG. 8 Production of anti-peptide antisera against ADAM8 and ADAM15 and their use to detect expression of ADAM8 (and induction by LPS and IFN-γ) and ADAM15 in human THP-1 cells FIG. 9 Summary diagram of the production and consequences of soluble CD23.
Figure 9:
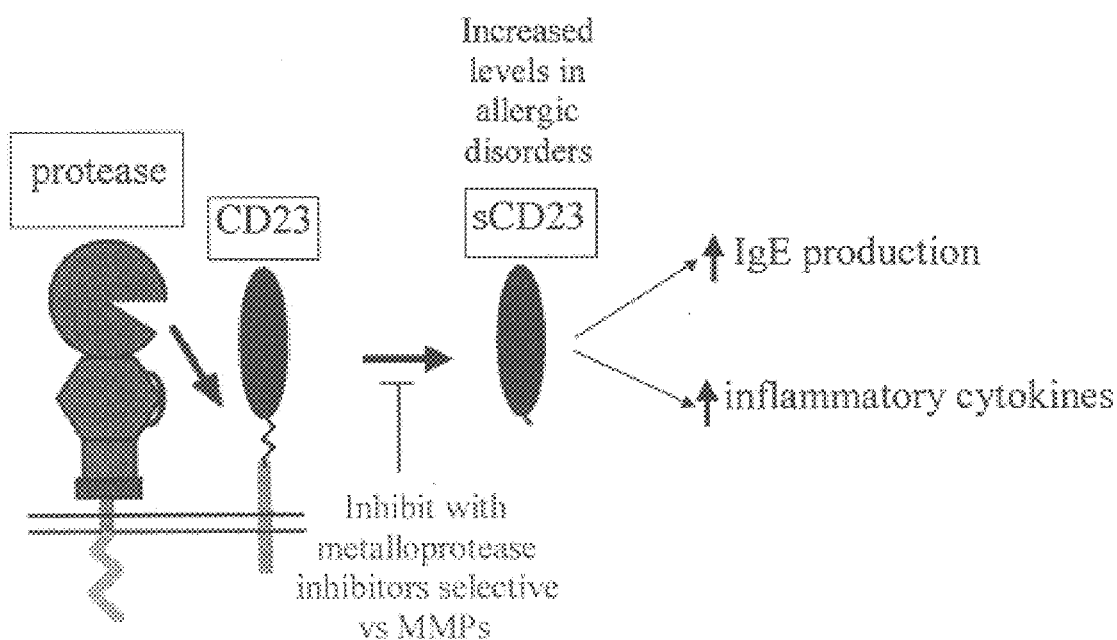

Polyclonal antisera against ADAM8 and ADAM15 were generated by immunizing rabbits with KLH-conjugated peptides corresponding to the C-terminal sequences of ADAM8 and 15, respectively. The antisera were used to detect ADAM8 and ADAM15 in THP-1 cell lysates. THP-1 cells were treated with interferon(IFN)-γ (200U/ml) or bacterial lipopolysaccharide (LPS) (100 ng/ml), for 24 hours or 16 hours, respectively. The cells were then harvested, washed with PBS and lysed in PBS containing 1% NP-40 and Complete® protease inhibitors. The cell extracts were analyzed for expression of ADAM8 and ADAM15 by SDS-PAGE, transfer to nitrocellulose, and immunoblotting with the antisera to ADAM8 and ADAM15, respectively. As seen in FIG. 8, ADAM8 is detected as a band migrating to approximately 70,000 daltons, and ADAM15 migrates to approximately 100,000 daltons, each representing the full-length protein (as compared to the smaller, soluble variants described above). The corresponding pre-immune sera gave no positive bands at these molecular weights for THP-1 cell extracts in similar assays.

Further, the detection by the specific antiserum showed that ADAM8 was up-regulated at the protein level approximately two-fold in response to LPS treatment, and approximately ten-fold in response to IFN-γ. In contrast, the antiserum to ADAM15 showed that no up-regulation of ADAM15 protein levels was evident in response to these agents.

EXAMPLE 6

CLEAVAGE OF CD23 FROM THE SURFACE OF THE U937 MACROPHAGE CELL LINE

Figure 10:
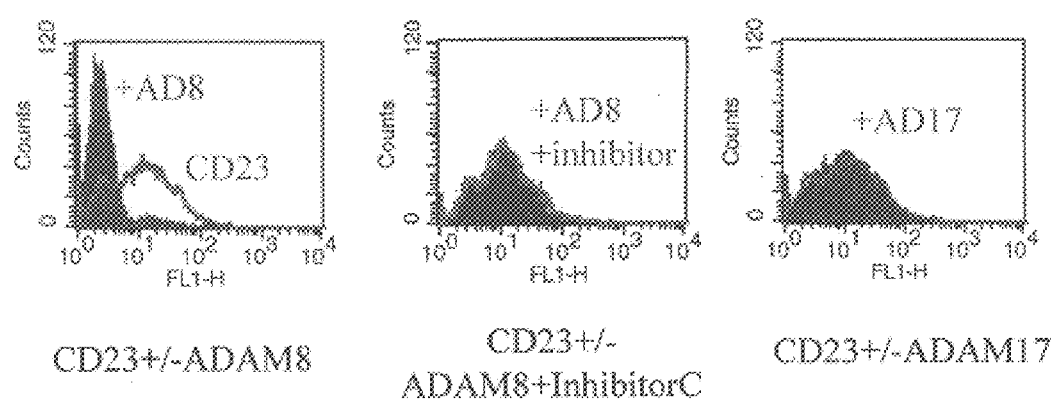
FIG. 10 Cleavage of membrane-bound CD23 on macrophage cell line by ADAM8.

U-937 (ATCC CRL-1593.2), a monoblastoid cell line, were harvested, washed and resuspended in HEPES-buffered saline, pH 7.5. Then the cells were treated for one hour at 37° C. in the absence or presence of ADAM8, ADAM17, ADAM15 or MDC-L. As a further control, some cells were incubated in the presence of ADAM8, ADAM17, ADAM15 or MDC-L with the addition of Inhibitor C. Intact, membrane-bound CD23 was then detected by staining the cells with a FITC-conjugated anti-human CD23 antibody (Pharmingen) and detection by flow cytometry. The results in FIG. 10 show that ADAM8 can effectively cleave CD23 from the surface of cells and that this process can be inhibited by Inhibitor C. ADAM15 and MDC-L were similarly found to cleave membrane-bound CD23. ADAM17, which displays a different substrate specificity does not cleave CD 23 from the cell surface.

REFERENCES:

Alderson, M. R., Tough, T. W., Ziegler, S. F. and Armitage, R. J. (1992) Regulation. of human monocyte cell-surface and soluble CD23 (Fc.epsilon.RII) by granulocyte-macrophage colony-stimulating factor and IL-3. *J. Immunol.*, 149, 1252–7.

Armant, M., Ishihara, H., Rubio, M., Delespesse, G. and Sarfati, M. (1994) Regulation of cytokine production by soluble CD23: costimulation of interferon gamma secretion and triggering of tumor necrosis factor alpha release. *J Exp. Med.*, 180, 1005–11.

Armant, M., Rubio, M., Delespesse, G. and Sarfati, M. (1995) Soluble CD23 directly activates monocytes to contribute to the antigen-independent stimulation of resting T cells. *J Immunol.*, 155, 4868–75.

Aubry, J. P., Pochon, S., Graber, P;, Jansen, K. U. and Bonnefoy, J. Y. (1992) CD21 is a ligand for CD23 and regulates IgE production. *Nature (London)*, 358, 505–7.

Bailey, S., Bolognese, B., Buckle, D. R., Faller, A., Jackson, S., Louis-Flamberg, P., McCord, M., Mayer, R. J., Marshall, L. A. and Smith, D. G. (1998) Hydroxamate-based inhibitors of low affinity IgE receptor (CD23) processing. *Bioorg. Med Chem. Lett.*, 8, 23–28.

Bailey, S., Bolognese, B., Faller, A., Louis-Flamberg, P., MacPherson, D. T., Mayer, R. J., Marshall, L. A., Milner, P. H., Mistry, J., Smith, D. G. and Ward, J. G. (1999) Selective inhibition of low affinity IgE receptor (CD23) processing: P1' bicyclomethyl substituents. *Bioorg. Med Chem. Lett.*, 9, 3165–3170.

Bansal, A. S., MacGregor, A. J., Pumphrey, R. S., Silman, A. J., Ollier, W. E. and Wilson, P. B. (1994) Increased levels of sCD23 in rheumatoid arthritis are related to disease status. *Clinical and Experimental Rheumatology*12, 281–5.

Beguin, Y., Lampertz, S., De Groote, D., Igot, D., Malaise, M. and Fillet, G. (1993) Soluble CD23 and other receptors (CD4, CD8, CD25, CD71) in serum of patients with chronic lymphocytic leukemia *Leukemia*7, 2019–25.

Bohm, B. B., Aigner, T., Gehrsitz, A., Blobel, C. P., Kalden, J. R. and Burkhardt, H. (1999) Up-regulation of MDC15 (metargidin) messenger RNA in human osteoarthritic cartilage. *Arthritis Rheum.*, 42, 1946–1950.

Buroker-Kilgore, M. and Wang, K. K. W. (1993) A Coomassie Brilliant Blue G-250-based colorimetric assay for measuring activity of calpain and other proteases. *Anal. Biochem.*, 208, 387–92.

Chomarat, P., Briolay, J., Banchereau, J. and Miossec, P. (1993) Increased production of soluble CD23 in rheumatoid arthritis, and its regulation by interleukin-4. *Arthritis And Rheumatism*36, 234–42.

Christie, G., Barton, A., Bolognese, B., Buckle, D. R., Cook, R. M., Hansbury, M. J., Harper, G. P., Marshall, L. A., McCord, M. E., Moulder, K., Murdock, P. R., Seal, S. M., Spackman, V. M., Weston, B. J. and Mayer, R. J. (1997) IgE secretion is attenuated by an inhibitor of proteolytic processing of CD23 (FC.epsilon.RII). *Eur. J Immunol.*, 27, 3228–3235.

Coolican, S. A., Haiech, J. and Hathaway, D. R. (1986) The role of subunit autolysis in activation of smooth muscle Ca2+-dependent proteases. *J Biol. Chem*, 261, 4170–6.

Corominas, M., Mestre, M., Bas, J., Verdaguer, J., Valls, A., Romeu, A. and Buendia, E. (1993) CD23 expression on B-lymphocytes and its modulation by cytokines in allergic patients. *Clinical And Experimental Allergy*23, 612–7.

Corry, D. B. and Kheradmand, F. (1999) Induction and regulation of the IgE Response. *Nature*, 402, B18–B23.

Dasic, G., Juillard, P., Graber, P., Herren, S., Angell, T., Knowles, R., Bonnefoy, J.-Y., Kosco-Vilbois, M. H. and Chvatchko, Y. (1999) Critical Role of CD23 in Allergen-induced Bronchoconstriction in a Murine Model of Allergic Asthma. *Eur. J Immunol.*, 29, 2957–2967.

Di Lorenzo, G., Drago, A., Pellitteri, M. E., Candore, G., Colombo, A., Potestio, M., Di Salvo, A., Mansueto, S. and Caruso, C. (1999) Serum levels of soluble CD23 in patients with asthma or rhinitis monosensitive to Parietaria. Its relation to total serum IgE levels and eosinophil cationic protein during and out of the pollen season. *Allergy And Asthma Proceedings*20, 119–25.

Dine, G., Culioli, B., Rehn, Y. and Brahimi, S. Serum assay of soluble CD23: value in chronic lymphoid B-cell leukemia (letter). *Presse Medicale*25, p. 864.

Herren, B., Raines, E. W. and Ross, R. (1997) Expression of a disintegrin-like protein in cultured human vascular cells and in vivo. *Faseb J*, 11, 173–180.

Howard, L., Nelson, K. K., Maciewicz, R. A. and Blobel, C. P. (1999) Interaction of the metalloprotease disintegrins MDC9 and MDC15 with two SH3 domain-containing proteins, endophilin I and SH3PX1. *J Biol. Chem.*, 274, 31693–31699.

Kataoka, M., Yoshiyama, K., Matsuura, K., Hijiya, N., Higuchi, Y. and Yamarnoto, S. (1997) Structure of the murine CD156 gene, characterization of its promoter, and chromosomal location. *J Biol. Chem.*, 272, 18209–18215.

Knauf, W. U., Langenmayer, I., Ehlers, B., Mohr, B., Adorf, D., Nerl, C. H., Hallek, M., Zwingers, T. H., Emmerich, B. and Thiel, E. (1997) Serum levels of soluble CD23, but not soluble CD25, predict disease progression in early stage B-cell chronic lymphocytic leukemia. *Leuk. Lymphoma*, 27, 523–532.

Letellier, M., Sarfati, M. and Delespesse, G. (1989) Mechanisms of formation of IgE-binding factors (Soluble CD23) - I. FceRII bearing B cells generate IgE-binding factors of different molecular weights. *Mol. Imm.*, 26, 1105–1112.

Lonergan, S. M., Johnson, M. H. and Calkins, C. R. (1995) Improved calpain assay using fluorescein isothiocyanate-labeled casein. *J Food Sci.*, 60, 72–3.

Marolewski, A. E., Buckle, D. R., Christie, G., Eamshaw, D. L., Flamberg, P. L., Marshall, L. A., Smith, D. G. and Mayer, R. J. (1998) CD23 (Fc.epsilon.RII) release from cell membranes is mediated by a membrane-bound metalloprotease. *Biochem. J*, 333, 573–579.

McGeehan, G. M., Becherer, J. D., Moss, M. L., Schoenen, F. J., Rocque, W. J., Chen, W.-J., Didsbury, J. R. and Jin, S.-L. C. (i 997) Mammalian tumor necrosis factor .alpha. convertase, recombinant expression and purification, and screening for hydroxamic acid derivatives or other inhibitors useful for disease treatment. *PCT Int. Appl.* (Glaxo Group Limited, UK; McGeehan, Gerard M.; Becherer, James David; Moss, Marcia L.; Schoenen, Frank J.; Rocque, Warren J.; Chen, Wen-Ji; Didsbury, John R.; Jin, Shiow-Lian Catherine). WO9735538

Melewicz, F. M., Kline, L. E., Cohen, A. B. and Spiegelberg, H. L. (1982) Characterization of Fc Receptors for IgE on Human Alveolar Macrophages. *Clin, Exp. Immunol.*, 49, 364–370.

Monteseirin, J., Llamas, E., Munoz, F., Bandres, F., Bono, M. J. and Conde, J. (1993) Production of soluble CD23 from peripheral blood lymphocytes of asthmatic patients. *Allergologia Et Immunopathologia*21, 75–8.

Nath, D., Slocombe, P. M., Stephens, P. E., Warn, A., Hutchinson, G. R., Yamada, K. M., Docherty, A. J. P. and Murphy, G. (1999) Interaction of metargidin (ADAM-15) with avb3 and a5b1 integrins on different hemopoietic cells. *J. Cell Sci.*, 112, 579–587.

Ng, M. and Auld, D. S. (1989) A fluorescent oligopeptide energy transfer assay with broad applications for neutral proteases. *Anal. Biochem.*, 183, 50–6.

Ribbens, C., Bonnet, V., Kaiser, M. J., Andre, B., Kaye, O., Franchimont, N., De Groote, D., Beguin, Y. and Malaise, M. G. (2000) Increased synovial fluid levels of soluble CD23 are associated with an erosive status in rheumatoid arthritis (RA). *Clin. Exp. Immunol.*, 120, 194–199.

Roberts, C. M., Tani, P. H., Bridges, L. C., Laszik, Z. and Bowditch, R. D. (1999) MDC-L, a novel metalloprotease disintegrin cysteine-rich protein family member expressed by human lymphocytes. *J Biol. Chem.*, 274, 29251–29259.

Roghani, M., Becherer, J. D., Moss, M. L., Atherton, R. E., Erdjument-Bromage, H., Arribas, J., Blackburn, R. K., Weskamp, G., Tempst, P. and Blobel, C. P. (1999) Metalloprotease-disintegrin MDC9: intracellular maturation and catalytic activity. *J Biol. Chem.*, 274, 3531–3540.

Sano, H., Munoz, N. M., Sano, A., Zhu, X., Herrnreiter, A., Choi, J. and Leff, A. R. (1999) Upregulated Surface Expression of Intracellularly Sequestered IgE Receptors (FcERII/CD23) Following Activation in Human Peripheral Blood Eosinophils. *Proc. Assoc. Amer. Phys.*, 111, 82–91.

Sekut, L. and Connolly, K. (1998) AntiTNF-.alpha. agents in the treatment of inflammation. *Expert Opin. Invest. Drugs, Vol.* 7, pp. 1825–1839.

Twining, S. S. (1984) Fluorescein isothiocyanate-labeled casein assay for proteolytic enzymes. *Anal. Biochem.*, 143, 30–4.

Wadstroem, T. and Smyth, C. J. (1973) Zymogram methods applied to thin-layer isoelectric focusing in polyacrylamide gel. *Sci. Tools, Vol.* 20, pp. 17–21.

Wheeler, D. J., Parveen, S., Pollock, K. and Williams, R. J. (1998) Inhibition of sCD23 and immunoglobulin E release from human B cells by a metalloproteinase inhibitor, GI 129471. *Immunology*, 95, 105–110.

Yamamoto, S., Higuchi, Y., Yoshiyama, K., Shimizu, E., Kataoka, M., Hijiya, N. and Matsuura, K. (1999) ADAM family proteins in the immune system. *Immunol. Today, Vol.* 20, pp. 278–284.

Yanagihara, Y., Sarfati, M., Marsh, D., Nutman, T. and Delespesse, G. (1990) Serum levels of IgE-binding factor (soluble CD23) in diseases associated with elevated IgE. *Clinical And Experimental Allergy* 20, 395–401.

Yu, P., Kosco-Vilbois, M., Richards, M., Koehler, G. and Lamers, M. C. (1994) Negative feedback regulation of IgE synthesis by murine CD23. *Nature (London)*, 369, 753–6.

Zhang, X.-P., Kamata, T., Yokoyama, K., Puzon-Mclaughlin, W. and Takada, Y. (1998) Specific interaction of the recombinant disintegrin-like domain of MDC-15 (metargidin, ADAM-15) with integrin avb3. *J Biol. Chem.*, 273, 7345–7350.

What is claimed is:

1. An in vitro method to detect inhibition of enzymatic activity of metalloproteases comprising:
   a) combining enzyme protein selected from the group consisting of ADAM8, ADAM15 and MDC-L, and a peptide substrate comprising a detectable label wherein said substrate is selected from the group of amino acid sequences consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 in the presence or absence of a test compound;
   b) incubating the reaction mixture of (a) for sufficient time to produce a detectable product as a result of enzymatic activity upon the substrate; and
   c) measuring the quantity of the product formed in the presence of the tested compound and in its absence, whereby the inhibition is detected when the amount of product formed in the presence of the test compound is less than that in the absence of said test compound.

2. An in vitro method to detect compound inhibition of enzymatic activity of metalloproteases comprising:
   a) combining enzyme protein selected from the group consisting of ADAM8, ADM15 and MDC-L, and a peptide substrate comprising a detectable label wherein said substrate is selected from the group of amino acid sequences consisting of SEQ ID NO: 1, SEQ ID NO: 2, SEQ ID NO: 3, and SEQ ID NO: 8 in the presence or absence of a test compound;
   b) incubating the reaction mixture of (a) the for sufficient time to produce a detectable product as a result of enzymatic activity upon the substrate; and
   c) measuring the quantity of the product formed in the presence of the tested compound and in its absence, whereby the inhibition is detected when the amount of product formed in the presence of the test compound is less than that in the absence of said test compound.

3. The method of claim 1 or 2 wherein the peptide substrate comprises a detectable label selected from the group consisting of $^{125}$I, $^{131}$I, $^{3}$H, $^{14}$C, $^{35}$S, $^{32}$P, 33P, a fluorescent dye, or calorimetric indicator.

4. The method of claim 1 or 2 wherein the peptide substrate comprises a fluorophore and a quencher or acceptor located at opposite ends of the cleavage site of the substrate peptide.

* * * * *